United States Patent [19]
Hirota et al.

[11] Patent Number: 6,005,962
[45] Date of Patent: Dec. 21, 1999

[54] PERSONAL IDENTIFICATION SYSTEM

[75] Inventors: Atushi Hirota, Sagamihara; Yukihiro Kawano, Tokyo; Takeo Juji, Matudo; Kei Takahashi, Hachioji, all of Japan

[73] Assignee: Kawasumi Laboratories, Inc., Tokyo, Japan

[21] Appl. No.: 08/668,924

[22] Filed: Jun. 24, 1996

[30] Foreign Application Priority Data

Jun. 26, 1995 [JP] Japan ................................... 7-182067
Mar. 27, 1996 [JP] Japan ................................... 8-097573

[51] Int. Cl.⁶ .................................................. G06K 9/00
[52] U.S. Cl. ............................................................ 382/124
[58] Field of Search ............................... 382/115, 116, 382/118, 119, 124, 125, 126, 127, 128, 232, 100, 312; 356/71; 364/468.22, 478.1; 283/81, 68, 69, 74, 75, 78; 380/51; 340/573; 235/462

[56] References Cited

U.S. PATENT DOCUMENTS

| | | | |
|---|---|---|---|
| 5,071,168 | 12/1991 | Shamos | 283/117 |
| 5,193,855 | 3/1993 | Shamos | 283/117 |
| 5,381,487 | 1/1995 | Shamos | 382/2 |
| 5,505,494 | 4/1996 | Belluci et al. | 283/75 |
| 5,592,561 | 1/1997 | Moore | 283/103 |
| 5,611,051 | 3/1997 | Pirelli | 395/210 |
| 5,623,552 | 4/1997 | Lane | 382/124 |
| 5,635,012 | 6/1997 | Belluci et al. | 156/277 |

FOREIGN PATENT DOCUMENTS

6343679   6/1994  Japan .
6-343679 12/1994  Japan .

Primary Examiner—Joseph Mancuso
Assistant Examiner—Brian P. Werner
Attorney, Agent, or Firm—Micheal J. Striker

[57] ABSTRACT

A personal identification system for collating an article requiring personal identification with a person using the article has a personal identification data reader for reading the image of a characteristic portion of a human body capable of identifying a person such as his fingerprint and digitizing the image data. Moreover, the system has a label printer for printing the personal identification data on a label as two-dimensional data codes and the personal identification data printed on the label is read by a label data reader serving as a two-dimensional data code reader. The personal identification data read by the personal identification data reader and acceptance or rejection of the collation result is decided. These operation histories are recorded and preserved in a hard disk.

2 Claims, 6 Drawing Sheets

PERSONAL IDENTIFICATION SYSTEM

BACKGROUND OF THE INVENTION

The present invention relates to a personal identification system for comparing an article to which personal identification should be applied with a person using the article, for example for collating previously collected and preserved blood with the blood of a patient (donor) and confirming whether the stored blood is his own when the patient undergoes a surgical operation and uses the stored blood for transfusion.

The official gazette of Japanese Patent Laid-Open No. 343679/1994 (Japanese Patent Application No. 164047/1993) discloses a blood bag control method for performing self-blood transfusion. This system uses a card of a patient in which predetermined information such as the patient's code number, address, name, age, date of birth, body weight, type of blood, (ABO.Rh way), biochemical inspection items, presence or absence of infectious disease and type of them if any, and name of disease. Further the system uses a storage container for storing a blood bag which is provided with an electronic locking device. The electronic locking device is unlocked and a blood bag can be taken out from the storage container when the label of a card (e.g. clinical chart) of a patient is collated with the label of the storage container and coincides each other. Moreover, the above official gazette describes that the label attached to the taken-out blood bag is collated with the label of the patient's card to confirm them, the signature of the patient and the photograph of the patient's face are used, and a bar code is used for processing of the data of personal identification.

The above blood bag control system has the following problems:

1. In the case of collation according to the photograph of the patient's face, imperfect collation may occur due to change of the patient's face because of hospital treatment, change of the patient's face because of patient's anesthetic state, resemblance between strangers, or deterioration of the photograph due to a preservation temperature.

2. In the case of collation according to the signature of the patient, imperfect collation may occurred due to a physical condition of the patient, erroneous decision of the patient due to his anesthetic state, a case in which the patient cannot sign because of his invalid hand or finger, or presence of another patient with the same first and second names.

3. In the case of collation according to the control card of the patient, imperfect collation may occur due to a case in which the patient does not have his card when he undergoes a surgical operation or a case in which patient's cards are confused (though a method of embedding a non-contact information identification device using electromagnetic waves in the body of a patient is recently developed, there is a problem in view of morals).

Moreover, if the above items 1 and 3 are accidentally overlapped, patients are confused in the worst case and the blood of other person may be transfused under a state in which a patient cannot identify his own signature. It is the biggest problem of the above control system that a patient himself (individual) is not collated with an article to be identified (e.g. blood bag).

A bar code for processing the data for personal identification is widely used for supermarkets, retailers, OA, FA, medical treatment, libraries, and home delivery service, in which a numerical or alphabetical character is expressed in accordance with combination of widths of a white portion (space) and black portion (bar). However, the bar code has a low information density. Therefore, it is not realistic to bar-code personal identification data such as a fingerprint, palm shape, finger shape, or ear shape because it requires a large amount of data.

SUMMARY OF THE INVENTION

Accordingly it is an object of the present invention to provide a personal identification system which is formed so as to securely execute collation and confirmation of an article requiring personal identification and a person using the article and having a low risk about disappearance or quality change of data.

It is another object of the present invention to provide a personal identification system which is formed so that it does not require IC card or memory card, and safely and securely executes collation and confirmation by using a characteristic portion of a human body such as a fingerprint as personal identification information.

It is still another object of the present invention to provide a personal identification system capable of clarifying the responsibility of an operator by recording and preserving a series of operation processing information.

In keeping with these objects and with others which will become apparent hereinafter, one feature of the present invention resides, briefly stated, in a personal identification system of the present invention comprises means for reading personal identification data obtained by reading the image of a characteristic portion of a human body capable of identifying a person and processing the image; personal identification data entry means having data record and preservation means for recording and preserving the operation history of the system and printing means for printing personal identification data read by the personal identification data read means on a label; and personal identification data collation means which has label data read means for reading the personal identification data of the label attached to the article and collates the personal identification data of the label read by the label data rad means with the personal identification data read by the personal identification data read means to decide acceptance or rejection of the collation result.

According to one embodiment of the present invention, the personal identification data is obtained by reading the image of a fingerprint, palm shape, finger shape, or ear shape and digitizing the data and the label printing means outputs the personal identification data as two-dimensional data codes. Moreover, the label data read means serves as a two-dimensional code reader.

The novel features which are considered as characteristic for the present invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

Figure 1:
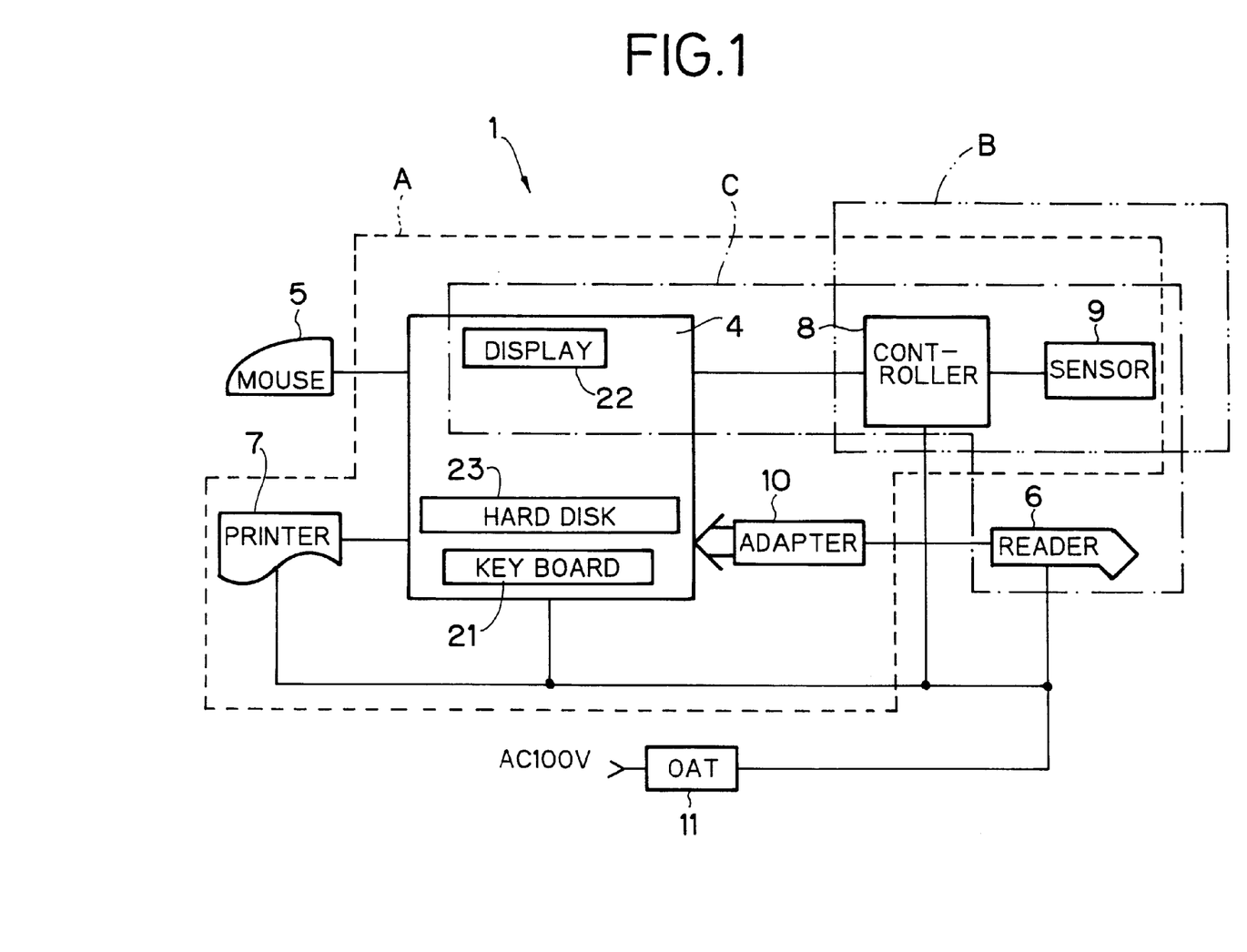
FIG. 1 is a block diagram for explaining the basic structure of a personal identification system of the present invention.

A personal identification system 1 of the present invention is shown in a block diagram of FIG. 1 with main units including a computer 4, personal identification data readers 8 and 9 (personal identification data read means) having a sensor section 9 and a controller section 8, a label data reader 6 (label data read means), and a label printer 7 (printing means).

In this embodiment, personal identification data entry means A includes the computer 4, personal identification data readers 8 and 9, and label printer 7. Personal identification data read means B includes the personal identification data readers 8 and 9. Moreover, personal identification data collation means C (personal identification data collation means having label data read means for reading personal identification data of the label attached to the article and collating the personal identification data of the label read by the label data read means with the personal identification data read by the person identification data read means to decide acceptance or rejection of the collation result) includes the label reader 6, personal identification data readers 8 and 9, and computer 4. In the case of this embodiment, the means A, B, and C are united.

The computer 4 collates inputted personal identification data, records and preserves various data values, and reads data. Therefore, though it is preferable to use a so-called personal computer, an optimum computer is selected correspondingly to data quantity or data control scale.

The computer 4 has a voice generating function and has a keyboard 21 (personal identification input means) for inputting personal identification such as the patient's code number, address, name, age, date of birth, body weight, type of blood (ABO.rh way), biochemical inspection items, presence or absence of and type of infectious disease, and name of disease. The computer 4 has also a hard disk 23 (data storage and preservation means) for recording and preserving the operation history, collation confirmation history, and transfusion history of the personal idenification system, personal identification data, and personal information, a data display 22 (data display means) for displaying a collation result of personal information and personal identification data on a display such as a CRT or LCD, and a mouse 5 for executing program of the computer 4.

The identification data reader sensor section 9 reads the image (picture) of a characteristic portion of a human body capable of identifying a person, such as, for example, a fingerprint, palm shape, finger shape, or ear shape, and which may be used an image reader such as a CCD or scanner. The identification data reader controller section 8 has a function for digitizing an image signal read by the sensor section 9 (an electronic picture is digitized and converted to a mathematical characterization). The digitization and conversion of the image signal read by the sensor section 9 may be executed by the computer 4. In this case, the controller 8 is unnecessary.

The label data reader 6 is a unit for reading personal identification data printed on a label attached to a blood bag, which uses a two-dimensional data code reader in the case of the present invention. As the reader 6, it is preferable to use a video camera (industrial video camera, machine vision camera, CCD policing camera, portable vide camera, still video camera, or portable wand), which easily interlocks with an electronic locking device. A read signal of the label data reader 6 is input to the computer 4 through an adapter 10.

A two-dimensional data code (matrix data code) is not a mere symbol but a computer language consisting of white and black cells, which is a two-dimensional matrix code dynamically variable correspondingly to actually coded information and whose size can be selected in a range between 14" and 0.001" squares. That is, the information density is high and the misreading rate is as low as 1/65,000,000

The label printer 7 is used to print the data for personal identification (including other personal information) on a label. The data is obtained by combining the personal identification data digitized by the controller section 8 or the computer 4, with the personal identification recorded and preserved in the computer 4. The combined data are converted to two-dimensional data codes by the computer 4. It is better to print other personal information in the form of normal characters so as to raise the visibility of an operator.

Printed data codes can optionally be combined in color as long as there is a contrast of approx. 20%. As a printer for the printed data codes, it is preferable to use a dot printer, ink jet printer, or laser printer. Moreover, it is possible to select a label forming machine, laser beam, chemical etching, lithography, flexography, or photoengraving according to necessity.

Because a method for digitizing personal identification with other personal information are secret, it is impossible for a third person to reproduce personal identification data and an picture signal from two-dimensional data codes printed on a label. Therefore, privacy can completely be protected.

The power supply of a personal identification system 1 uses a commercial power supply and its electric power is distributed by a tap 11 and thereafter fed to the computer 4, label data reader 6, personal identification data reader controller 8, and label printer 7. It is also possible to feed electric power by a battery.

The united personal identification system 1 of FIG. 1 can independently be used by moving the system 1 between a control room 40, a blood collection room 41, and a surgical operation room 42. However, to perform operations efficiently, it is also possible to use a plurality of personal identification systems so that personal identification data entry, personal identification data read, and personal identification data collation are separately performed by the systems.

Figure 2:
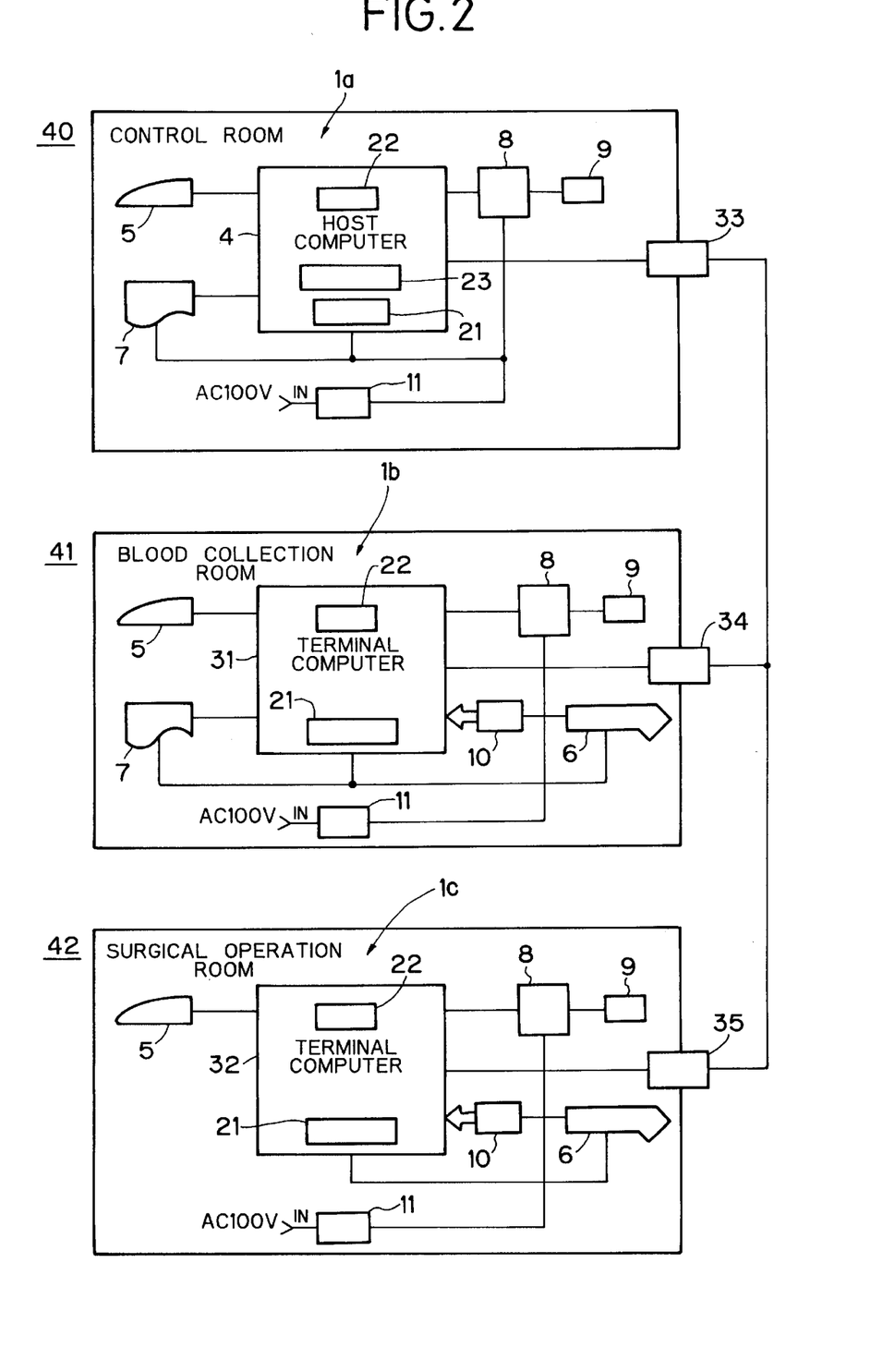
FIG. 2 is a block diagram for explaining an embodiment of a personal identification system of the present invention.

A personal identification system 1a in accordance with the embodiment of FIG. 2 for using exclusively personal identification data entry is placed in control room 40, a personal identification system 1b for using exclusively personal identification data read is placed in the blood collection room 41, and a personal identification system 1c for using exclusively personal identification data collation is placed in the surgical operation room 42.

The personal identification system 1a in the control room 40 omits the label data reader 6 and the adapter 10 shown in FIG. 1. The personal identification system 1b in the blood collection room 41 omits the hard disk 23. Moreover, the personal identification system 1c in the surgical operation room 42 omits the label printer 7.

In this embodiment, the computer 4 of the personal identification system 1a in the control room 40 works as a host computer. Also the computers 31 and 32 placed in the blood collection room 41 and surgical operation room 42 work a terminal computers. The host computer 4 connects with the terminal computers 31 and 32 through modems (data transmission/reception means) 33, 34, and 35.

In the embodiment of FIG. 2., various pieces of information such as personal identification data, personal information, and operation histories are centrally controlled by the hard disk 23 of the computer 4 in the control room 40. That is, the recorded and preserved data used for execution in the blood collection room 41 and surgical operation room 42 is received from the hard disk 23. And also the data used for execution in the blood collection room 41 and surgical operation room 42 is received from the hard disk 23. And also the data input through the keyboards 21 and 21 in the blood collection room 41 and surgical operation room 42, and the label data records read by the label data readers 6 and 6 are transmitted to the hard disk 23 of the personal identification system 1a through the modems 33, 34, and 35.

Figure 3:
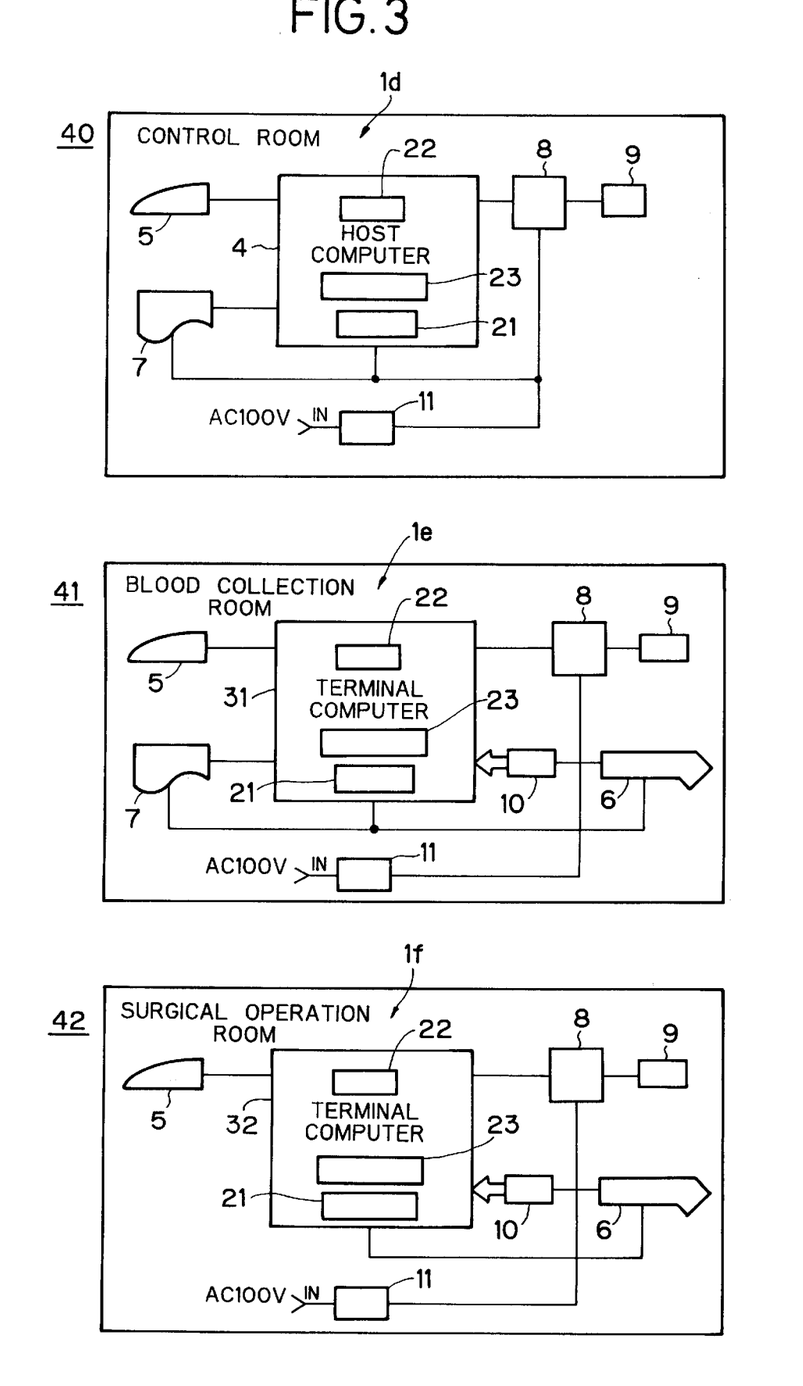
FIG. 3 is a block diagram for explaining another embodiment of a personal identification system of the present invention.

Another embodiment of the present invention. This embodiment is different from the embodiment of FIG. 2 in that the computers 31 and 32 of personal identification systems 1e and 1f in the room 41 and 42 are provided with the hard disks 23 and 23 respectively, but they omit the modems 33, 34, and 35. This embodiment can independently operate the personal identification systems 1a, 1b, and 1c. However, it is necessary to regularly update the information preserved in the hard disks 23, 23, and 23 of personal identification systems 1a, 1b, and 1c in order to unify the information.

Figure 4:
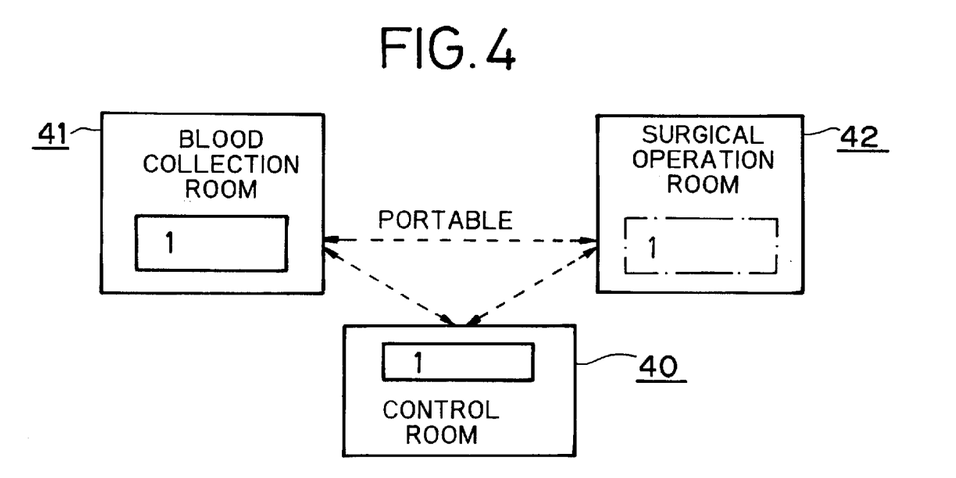
FIG. 4 is an illustration when using a personal identification system of the present invention for self-blood transfusion.

In the embodiment of FIGS. 3 and 4, various pieces of information such as patient's personal identification data and personal information, and operation histories are recorded and preserved in the personal identification system 1d in the control room 40 and printed on a label (to be attached to a clinical chart) by the label printer 7. Thereafter, bringing the label into the blood collection room 41, and there, the personal identification data of a patient (donor) is read by the label data reader 6 and collated the data with the patient himself. Also, a label data (printed by the label printer 7 in the room 41 and attached to a blood bag) can be read by the label data reader 6 in the room 41 and collate the data with the patient himself. Furthermore, the label, printed by the label printer 7 in the room 41, is attached to the blood bag, and collected a blood from the patient in the blood bag, and bringing the bag into surgical operation room 42, and there, the data on the label is read by the label data reader 6, and collated the data with the patient himself.

Figure 5:
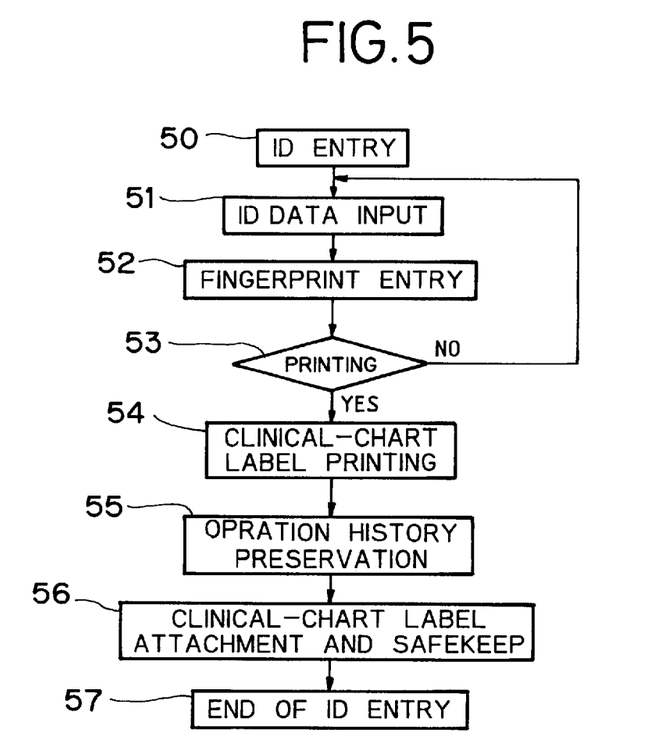
FIG. 5 is a flow chart showing ID entry steps when using a personal identification system of the present invention for self-blood transfusing.
Figure 6:
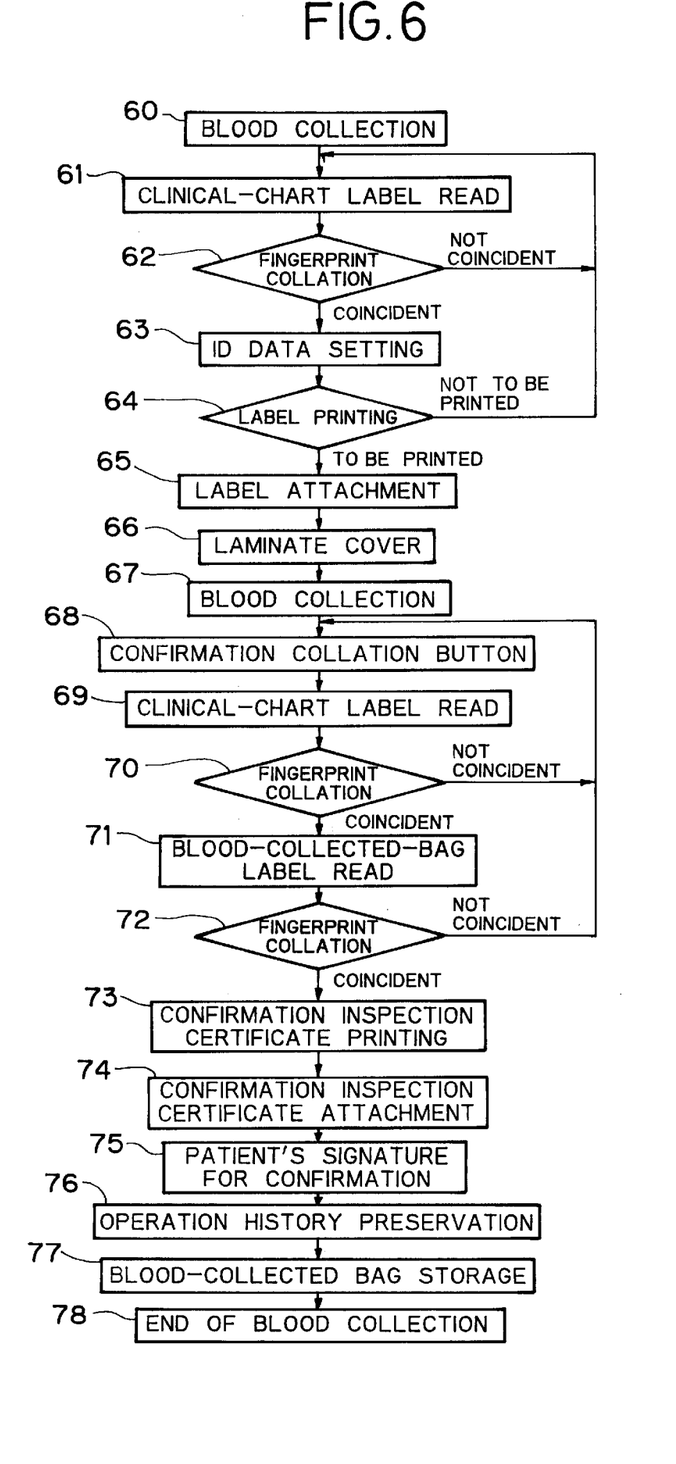
FIG. 6 is a flow chart showing blood-collection steps when using a personal identification system of the present invention for self-blood transfusion.
Figure 7:
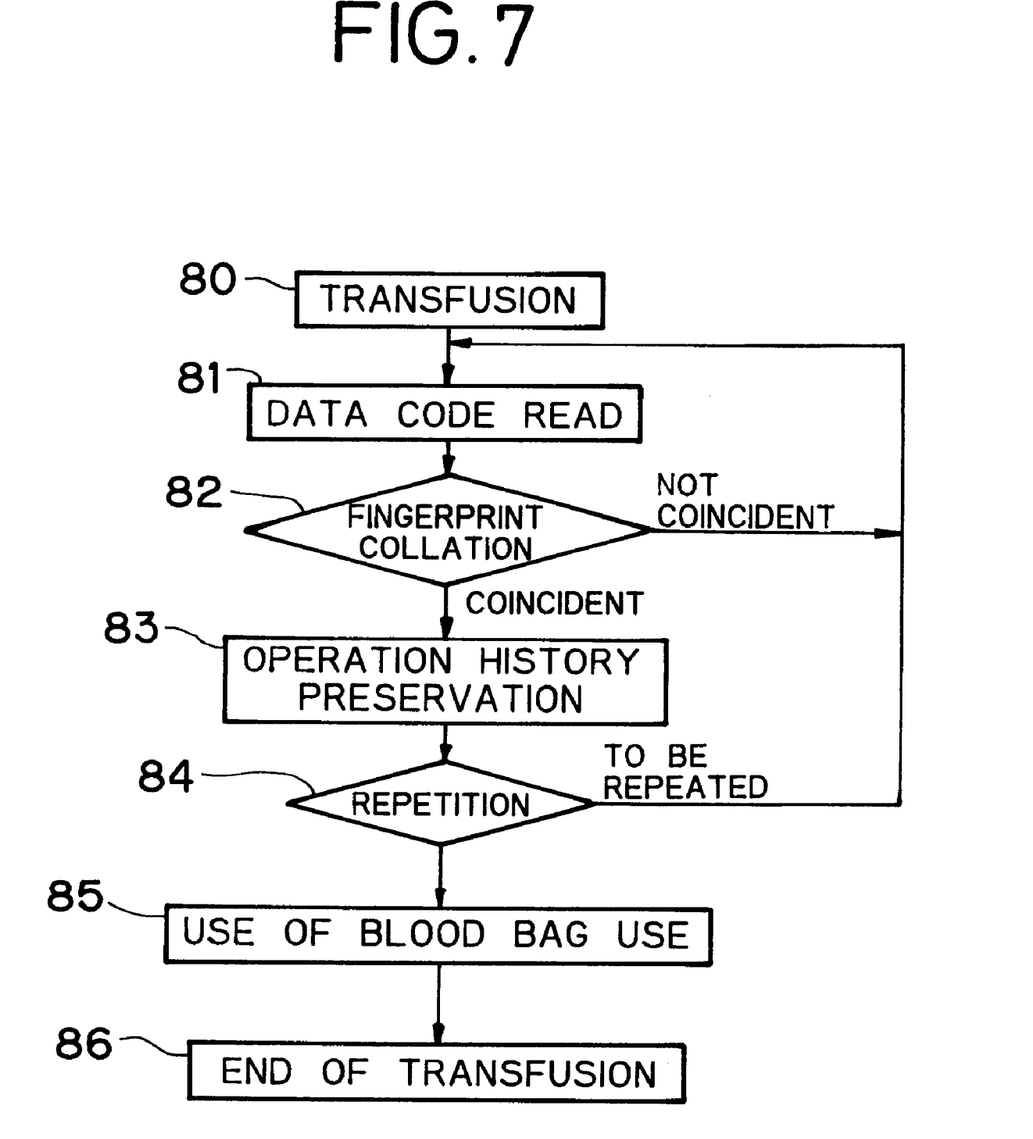
FIG. 7 is a flow chart showing transfusion steps when using a personal identification system of the present invention for self-blood transfusion.

Flow charts of operating process when using a personal identification system 1 of the present invention for self-blood translation or show in FIGS. 5–7. In these flow charts, a fingerprint is used as a personal identification data.

FIG. 5 shows a flow chart when entering the ID of a patient as a preliminary step of a medical treatment, in which a clinical chart of the patient is prepared and then ID entry is started (step 50). The ID entry is performed by inputting pieces of personal information such as the patient's name, age, sex, type of blood, entry finger, and ID patient put his finger on the personal identification data reader sensor section 9 to read his fingerprint data (step 52). Then, it is selected whether to print ID data on a label is found in the notation of the name, operations are retried from step 51. When the notation is correct, the ID data output by the label printer 7 to print the clinical-chart label (step 54). When printing the label, fingerprint data is combined with the name, ID number, entry finger,-issue date, and others inputted through the keyboard, the label is printed with two-dimensional data codes, and pieces of personal information such as the name and entry finger are also printed by normal characters to secure the visibility of the operator. Thereafter, the operation history of a series of the above operations (input and output of the data) is recorded and preserved in the hard disk 23 (step 55) and the printed clinical-chart label is attached to the patient's clinical chart to preserve it (step 56). After the above series of operations, the ID entry is ended (step 57).

FIG. 6 shows flow chart for collecting the blood of a patient. Previous to start blood collection, the clinical chart which is attached the above label printed in the step 54 and an empty blood bag are prepared. Thereafter, blood collection is started (step 60).

First, the ID data is read out of the clinical chart label by the data reader 6 (the fingerprint data is read by the two-dimensional data code reader as the label data reader 6) (step 61). In the computer 4, the fingerprint data on the clinical chart label is collated with the patient's fingerprint read by the personal identification data reader sensor section 9, and output the result of acceptance or rejection to the display 22 and/or voices (step 62). If the data and the fingerprint do not coincide each other, they are reconfirmed and operations are retried from step 61 because the patient or the clinical chart may have been confused. When the data and the fingerprint coincide each other, ID data to be recorded on a label for a blood bag (blood-bag label) is input through the keyboard (step 63) and select whether to print the data (name, fingerprint data, quantity of blood to be collected and others) on the blood-bag label (step 64). When the data is imperfect, operations are retried from step 61. When printing the data, it is printed on the blood-bag label by the label printer 7. In this case, the ID data is printed in the form of two-dimensional data codes. The printed label is attached to the surface of an empty blood bag (step 65) and covered with a laminate to protect the surface (step 66). Thereafter, blood is collected in the blood bag from a patient (donor) (step 67).

After the above blood collecting, a confirmation-collation button of the controller 8 is pressed (step 68). By this operation, the fingerprint data printed on the clinical-chart label is read by the label data reader 6 (step 69) and collated with the fingerprint data of the patient (donor) read by the personal identification data reader sensor section 9 in the computer 4. Acceptance or rejection of the collation result is output to the display 22 and/or voices (step 70). If the both fingerprint data do not coincide each other as the result of collation, the clinical-chart is reconfirmed and operations are retried form step 68 because the patient or clinical-chart may be confused. When the both fingerprint data coincide each other, next, the fingerprint data printed on a label attached to the above blood bag is read by the label data reader 6, and collated with the fingerprint of a patient (donor) similarly to the above mentioned. Acceptance or rejection of the collation result is output to the display 22 and/or voices. If the fingerprint data do not coincide with the patient's fingerprint, they are reconfirmed and operations are retried from step 68 because the patient or blood bag filled with blood (step 75). Thereafter, the patient signs the signature space of the blood bag (step 75), and then, the above-mentioned series of operation histories and collation histories are recorded and preserved in the hard disk 23 (step 77). Finally, the above-mentioned confirmation inspection certificate and signature space are confirmed and the blood bag filled with the blood is stored in a predetermined place (step 77), and the blood collection is ended (step 78).

FIG. 7 shows a flow chart illustrating the operation procedure for transfusing the blood in the blood bag into a patient. Previous to start transfusion, the blood bag filled with blood through the above blood collection is prepared (step 80). Thereafter, the fingerprint data printed on the label of the blood bag is read by the label data reader 6 (step 81), and also, in the computer 4, the finger print data is collated with the fingerprint of a patient (donor) read by the section 9. Acceptance or rejection of the collation result is output to the display 22 and/or voices (step 82). If the fingerprint data do not coincide with the patient's fingerprint, operations are retried from step 81. When they coincide each other, the data, such as, operation history, collation confirmation history, transfusion history are recorded and preserved in the hard disk 23 (step 83). When blood is collected in a plurality of blood bags, operations from step 81 to step 83 are repeated for each blood bag (step 84). Thereafter, the blood in the blood bag is transfused to the patient (step 85) and transfusion is ended (step 86).

In this embodiments of FIGS. 2 and 3, the ID entry shown in FIG. 5 is exclusively executed by the personal identification systems 1a and 1d in the control room 40, and blood collection in FIG. 6 is exclusively executed by the personal identification systems 1b and 1e in the blood collection room 41. Moreover, the transfusion in FIG. 7 is exclusively executed by the personal identification systems 1c and 1f in the surgical operation room 42.

The present invention can effectively be used for the following cases:

1. When collating a patient with transfusion blood (patient's blood) at the time of a surgical operation and confirming them (ID: personal identification) in the before-operation blood-storing self-blood transfusion executed as a measure for preventing diseases which may be infected due to transfusion such as hepatitis, AIDS, and ALT or GVHD having a high death rate after transfusion.

2. When collating a patient with a clinical chart and/or the patient with a sickbed to confirm them in order to prevent an incorrect medical treatment due to confusion of the patient at the time of a surgical operation in a medical facility.

3. When collating a mother with a neonate to confirm them in order to prevent confusion of the neonate in a medical facility.

4. When collating a donor with a specimen (for preservation) of the donor to confirm them in a medical facility.

5. When collating a patient with an artificial dialyzer ( or artificial kidney) to confirm them in a medical facility in which the artificial dialyzer (or artificial kidney) is reused.

6. When collating an ID card and credit card with their owner to confirm them.

According to the above described invention, personal identification data (data obtained by digitizing a characteristic portion of a human body capable of identifying a person such as a fingerprint, palm shape, finger shape, or ear shape) is printed on a label, the label is attached to an article requiring personal identification, and the personal identification data printed on the label is collated with a person using the article and these are confirmed without using a storage medium such as a floppy disk, IC card, or memory card. Therefore, the risk of data disappearance is low and it is possible to securely perform personal identification. Moreover, because it is possible to record and preserve the fact that a person responsible for collation confirms acceptance or rejection of the collating result of a person with an article requiring personal identification in a computer, the responsibility on the PL law is clarified.

It will be understood that each of the elements described above, or two or more together, may also find a useful application in other types of constructions differeng from the types described above.

While the invention has been illustrated and described as embodied in personal identification system, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A personal identification system for self-blood transfusion, comprising a first room for controlling a patient's information, a second room for collecting blood from the patient into a blood bag, and a third room for transfusing the blood held in the bag into the patient, wherein the first room is provided with personal identification data read means for reading an image of a characteristic portion of a human body capable of identifying a person and digitizing the image; input means of personal information; means for combining personal identification data read by the personal identification data read means and personal information input by the input means, and converting to two-dimensional data code; printing means for printing the two-dimensional data code on a label for clinical chart; and data record and preservation means for recording and preserving information processing data including said personal identification data, personal information and operation history data; the second room is provided with label data read means for reading personal identification data from the label for the clinical chart printed in said first room; personal identification data read means for reading an image of a characteristic portion of a human body capable of identifying a person and digitizing the image; input means of personal information; personal identification data collation means for collating the personal identification data read by the label data read means with the personal identification data read by said personal identification data read means to decide acceptance or rejection of a collation result; and print means for converting the personal identification data read by the personal identification data read means and the personal information input by the input means to two-dimensional data code to print on the label for the blood bag; the third room is provided with label data read means for reading the personal identification data from the label of the blood bag collected in said second room; personal identification data read means for reading an image of a characteristic portion of a human body capable of identifying a person and digitalizing the image; and personal identification data collation means for collating the personal identification data on said label read by the label data read means with the personal identification data read by said personal identification data read means to decide acceptance or rejection of a collation result.

2. The personal identification system as defined in claim 1, wherein data sending and receiving means is provided for sending and receiving information processing data of the second and third rooms to and from the data memory and preservation means of the first room.

* * * * *